United States Patent [19]
Yanenko et al.

[11] Patent Number: 5,827,699
[45] Date of Patent: Oct. 27, 1998

[54] **STRAIN OF *RHODOCOCCUS RHODOCHROUS* AS A PRODUCER OF NITRILE HYDRATASE**

[75] Inventors: Alexandr Stepanovich Yanenko; Olga Borisovna Astaurova, both of Moscow; Sergei Petrovich Voronin, Saratov; Tatyana Vasilievna Gerasimova, Moscow; Nikolai Borisovich Kirsanov, Moscow; Vladimir Nikolaevich Paukov, Moscow; Inga Nikolaevna Polyakova, Moscow; Vladimir Georgievich Debabov, Moscow, all of Russian Federation

[73] Assignee: Gosudarstvenny. Nauchno-Issledovatelsky Institut Genetiki I Selektsii Promshlennykh Mikroorganizmov, Moscow, Russian Federation

[21] Appl. No.: 505,222

[22] PCT Filed: Dec. 15, 1994

[86] PCT No.: PCT/RU94/00275

§ 371 Date: Aug. 15, 1995

§ 102(e) Date: Aug. 15, 1995

[87] PCT Pub. No.: WO95/17505

PCT Pub. Date: Jun. 29, 1995

[30] Foreign Application Priority Data

Dec. 17, 1993 [RU] Russian Federation ........... 930556089

[51] Int. Cl.⁶ .......................... C12P 13/00; C12P 13/02; C12N 1/20
[52] U.S. Cl. ................ 435/129; 435/128; 435/252.1; 435/822; 435/183; 435/170

[58] Field of Search ...................... 435/128, 129, 435/252.1, 822, 170, 183

[56] References Cited

U.S. PATENT DOCUMENTS

| | | | |
|---|---|---|---|
| 4,248,968 | 2/1981 | Watanabe et al. | 435/129 |
| 4,555,487 | 11/1985 | Yamada et al. | 435/253.3 |
| 5,089,411 | 2/1992 | Yamada et al. | 435/244 |
| 5,179,014 | 1/1993 | Watanabe et al. | 435/129 |
| 5,200,331 | 4/1993 | Kawakami et al. | 435/129 |
| 5,206,158 | 4/1993 | Clifford et al. | 435/129 |
| 5,334,519 | 8/1994 | Yamada et al. | 735/129 |
| 5,352,828 | 10/1994 | Seki et al. | 564/4 |
| 5,356,801 | 10/1994 | Rambosek et al. | 735/195 |

FOREIGN PATENT DOCUMENTS

| | | |
|---|---|---|
| 0 109 083 B1 | 9/1986 | European Pat. Off. . |
| 0 362 829 | 4/1990 | European Pat. Off. . |
| 0 362 829 A2 | 4/1990 | European Pat. Off. . |
| 0 204 555 B1 | 5/1992 | European Pat. Off. . |
| 0 188 316 B1 | 10/1993 | European Pat. Off. . |
| 1731814 | 1/1993 | Russian Federation . |

*Primary Examiner*—David M. Naff
*Assistant Examiner*—Deborah Ware
*Attorney, Agent, or Firm*—Wigman, Cohen, Leitner & Myers, P.C.

[57] ABSTRACT

This invention provides a new strain *Rhodococcus rhodochrous* having a high nitrile hydratase activity and capable of hydrating aliphatic and aromatic nitriles to corresponding amides. An isolated culture of *Rhodococcus rhodochrous* VKM Ac-1515D is also disclosed for use in the production of nitrile hydratase. An enzymatic inducer is not required in the growth medium, however, the growth medium does include a salt, a carbon source, and a nitrogen source.

5 Claims, No Drawings

STRAIN OF *RHODOCOCCUS RHODOCHROUS* AS A PRODUCER OF NITRILE HYDRATASE

BACKGROUND OF THE INVENTION

1. Field of the Invention

The present invention relates to biotechnology and to preparing a new strain of bacteria having a high nitrile hydratase activity, which strain is intended for use in processes for producing amides from nitriles.

2. Description of Related Art

An enzyme of a nitrile hydratase capable to catalyze the conversion of nitriles into amides has been detected in a number of genera of bacteria. In order to produce nitrile hydratase in the process of growing bacteria, it is necessary to add an inducer to the nutrient medium. Nitriles and amides of organic acids (Ref. U.S. Pat. No. 4,555,487; European Patent No. 0 109 083; European Patent No. 0 204 555), urea or its derivatives (European Patent Application No. 0 362 829) may be used as inducers. Known in the prior art are strains of Corynebacterium N 774 (U.S. Pat. No. 4,248,968) and Rhodococcus sp. S-6 (U.S. Pat. No. 5,179,014) for which no inducer is required. Disadvantages of the strain N774 reside in its low nitrile hydratase activity (its specific activity is 50–60 units/mg, here and further on measured in mcM of acrylamide/min/mg of cells, based on dry matter weight), narrow range of substrate nitriles (only aliphatic nitriles), a low thermal stability of the enzymes (the optimum effect temperature for N774 is 35° C.). A disadvantage of the strain S-6 resides in its capacity to hydrate the produced amides to acids, whereby the quality of the amides is sharply affected. Furthermore, the strain S-6 has a low thermal stability of nitrile hydratase (not higher than 30 C.) and a low productivity (it is capable of accumulating not more than 20% of acrylamide in the solution). Expensive components of nutrient media (such as peptone, yeast extract, meat extract) are used to grow both strains, N774 and S-6.

In terms of its technical essence and the result achieved, the strain *Rhodoccus rhodochrous* J1 (European Patent Application No. 0 362 829) possessing a nitrile hydratase activity with respect to aliphatic and aromatic nitriles comes nearest to the present invention. However, the above-cited strain is disadvantageous by the fact that it is necessary to use a nutrient medium containing vitamins, yeast extract and peptone to cultivate it. Another disadvantage lies in the fact that the strain J1 necessitates the use of urea as inducer in high concentrations (7.5–12 g/l). Thus, when the strain is cultivated in a medium without urea, the specific nitrile hydratase activity is as low as 3.35 units/mg (total activity is 17.7 units/ml, here and further when measured in micromoles of acrylamide/min/ml of a cultural liquid). With the presence of 7.5 g/l of urea in the medium, the specific activity reaches 497 units/mg, the total activity being 2480 units/ml. It should be noted that the urea plays a dual role, namely: it is used as a source of nitrogen, and as an inducer for the nitrile hydratase. An amount of urea which does not exceed 2 g/l is sufficient for growth of the strain (whereby the specific nitrile hydratase activity of the strain J1 reaches 36.5 units/mg, the total activity being 189 units/ml), while high urea concentrations are necessary only for induction. For this reason, a substantial amount of the urea remains in the medium after cultivating therein the strain J1.

SUMMARY DESCRIPTION

It is the object of the present invention to produce a strain featuring a high nitrile hydratase activity, while being grown in simple synthetic media which does not contain any vitamins, amino acids, or other compounds serving as an inducer for synthesis of nitrile hydratase (nitriles, amides or urea).

The above-formulated object is accomplished by developing a strain *Rhodocosccus rhodochrous* M33 which would be capable in the absence of inducers to constitutively produce nitrile hydratase for catalyzing the hydrolysis of aliphatic nitriles, such as, e.g. acrylonitrile, and aromatic nitriles, such as, e.g. 3-cyano pyridine, into corresponding amides, such as, e.g. acrylamide and nicotinamide. The strain of the present invention is capable, in the absence of urea, to produce nitrile hydratase having a specific activity of 200–457 units/mg, and a total activity of 360–350 units/ml (depending on the carbon source used), and with 2 g/l of urea in the medium, of 180 units/mg and 1,368 units/ml, respectively. Another advantageous feature of the strain M33 resides in the practically complete absence of amidase activity. The point is that the amidase is an enzyme catalyzing hydrolysis of the produced amides into corresponding acids, e.g. acrylamide into acrylic acid, whereby the quality of the produced amides is sharply deteriorated.

The new strain grows in simple synthetic media comprising a carbon source, such as pyruvate, acetate or glucose, in concentrations of from 0.I to 4%, and a nitrogen source, such as ammonium, nitrate salts or urea, in concentrations of from 0.4 to 2%, no vitamins, amino acids, yeast extract being required for cultivation of the strain M33.

The *Rhodococcus rhodochrous* strain M33 is derived from the strain *Rhodococcus rhodochrous* M8 (RF Patent No. 1 731 814) by direct selection in two steps using selective media containing, chloracetamide, in the first stage, and acetamide, in the second stage.

The new strain in accordance with the present invention is capable of producing nitrile hydratase constitutively, in the absence of inducers, such as nitriles, amides or urea in the medium (Tab.1).

TABLE 1

| Cultivation conditions* | Specific activity Nitrile hydratase** | | Amidanse*** | |
|---|---|---|---|---|
| | M8 | M33 | M8 | M33 |
| Inducer-free medium | 8 | 457 | 0.0I | 0.00I |
| Medium with an inducer (urea, 10 g/l) | 315 | 425 | 0.3 | 0.015 |

*The strains were grown in Erlenmeyer flasks (750 ml volume), each containing 150 ml of a nutrient medium with pyruvate (5 g/l) and NH$_4$Cl (2 g/l) during 24 hours at 30° C., under intensive aeration conditions. Upon expiration of 24 hours, and the cultures thus prepared were divided into two parts and urea, as an inducer (in an amount of I0 g/l) was added to one of them, whereupon the cultivation procedure was continued for 48 hours more. Cells were isolated by centrifuging and used to determine the activities of the nitrile hydratase and amidase. The nitrile hydratase activity of each of the prepared cultures was determined using acrylonitrile as a substrate under standard conditions, whereas the amidase activity was determined by the formation of ammonium from acrylamide used as a substrate. The ammonium concentration was determined by the Nessler method.
**mcM of acrylamide/min/mg of cells, dry weight.
***mcM of ammonium/min/mg of cells, dry weight.

It is obvious from the above table, that the specific activity of the nitrile hydratase reaches 457 units/mg, when the strain M33 has been grown in a nutrient medium in the absence of urea. Under the same conditions, the nitrile hydratase activity of the original strain M8 is 8 units/mg. It is known that the specific activity of the nitrile hydratase strain J1, when grown in urea-free media, is 3.4 units/mg (Ref. European Patent Application No. 0 362 829; U.S. Pat. No. 5,089,411).

Thus, the strain M33, as distinct from the original strain M8 and strain J1, is capable of constitutively producing nitrile hydratase even in the absence of an inducer in the medium and has an amidase activity that is 20 times weaker.

The strain M33 has been deposited on Dec. 6, 1993 at the Institute of Biochemistry and Physiology of Microorganisms of The Russian Academy of Science (IBFM-VKM), Pushchino-na-Oke, 142292 Moscow Region, Russian Federation under accession number VKM Ac-1515 D in the All-Russian National Collection of Microorganisms and is characterized by the following morphologico-cultural and physiologico-biochemical characteristics:

Morphological properties. Cells of the strain M33 are nonmotile and gram-positive. No spores are produced, the cells are not acid resistant. At an age of 18–20 hours, the cells form long (up to 20 mcM), slightly ramified filaments which, after some 48–72 hours, undergo fragmentation into short rod- and cocci-shaped elements.

Cultural properties. After a 48-hour growth on glucose yeast extract agar belonging to dense nutrient media (such as MPA, Hottinger), the strain M33 produces round smooth colonies having a diameter of 1 mm and coloured from pale pink to pink-orange. When growth is carried out in a meat-peptone broth, a film and a sediment are formed, no changes in Litmus milk being observed.

Physiological properties. The strain represents an obligate aerobe, it reduces nitrates. MR and VP tests are negative. The strain generates hydrogen sulphide, it is oxidase negative, and catalase and phosphatase positive. The strain does not hydrolyze starch and cellulose, but it does hydrolyze Tween 60 and 80. No adenine is utilized. Cells are not resistant to heating in skim milk at 72° C. for 15 minutes. The strain M33 grows at pH 6–9 and at a temperature of 5–45 C. Acid is generated from the following sugars and alcohols: glucose, fructose, maltose, saccharose, sorbitol, mannitol, and glycerol. No gas generation is observed from a single sugar. It uses ammonium compounds, nitrates and urea as a single nitrogen source, while as a single carbon source, use is made of maltose, mannitol, sorbitol, glucose, glycerol, lactate, pyruvate, benzoate, p- and m-hydroxybenzoate, tyrosin. It does not use rhamnose, galactose, inositol, a-ketoglutarate.

Biochemical analysis has shown that the cell wall of the strain M33 contains meso-diaminopimelic acid, arabinose and galactose, which feature is characteristic of Coryneform bacteria having a Type IV cell wall. The cells also contain lipide A (LCH), which is characteristic of Rhodococci.

Thus, the strain M33 possesses characteristics which are typical of Coryneform bacteria. In view of the above-listed properties and in accordance with Bergy's Manual of Systematic Bacteriology and with Nesterenko's Classification Manual, the strain M33 can be related to the genus Rhodococcus, species *rhodochrous*.

To obtain M33 cells featuring a high nitrile hydratase activity, an M33 culture is placed into nutrient media, followed by incubation at 25°–30° C. for 24–72 hours.

Cell suspensions obtained by centrifuging the cultures, followed by resuspending the cells in a 10-mM phosphate buffer are used to transform the nitriles into amides.

The cells obtained by this procedure have a high nitrile hydratase activity and are capable of catalyzing hydrolysis of aliphatic and aromatic nitriles into corresponding amides over a wide range of temperatures extending from 4 to 50 C. and at pH values ranging from 3 to 10.

The standard test for measuring the nitrile hydratase activity is conducted in the following manner: 1 ml of a 2%-solution of nitrile in 10 mM of a phosphate buffer having a pH of 7.6 is mixed with 1 ml of a cell suspension containing 0.04 mg of cells based on the dry matter content. The reaction is conducted at 20° C. for 5 minutes, whereupon the reaction is stopped by adding 20 ml of concentrated HCl. The concentration of the amides thus-formed is determined by gas chromatography.

The nitrile hydratase activity is expressed in the following units:

One unit is defined as the amount of an enzyme required to produce amide from nitrile under the above-described conditions at a rate of 1 mcM/minute.

Specific activity is expressed in mcM amide/min/mg of cells, based on the dry matter content, or in units/mg;

Total activity is expressed in mcM amide/min/ml of the culture, or in units/ml.

DETAILED DESCRIPTION—EXAMPLE

Example 1 cells of strain M33 were cultivated in the absence of urea in a nutrient medium containing sodium nitrate as a nitrogen source. Five ml of a strain M33 culture, preliminarily grown in a medium of the following composition for 48 hours at 30° C., were placed into an Erlenmeyer flask (750 ml volume) filled with 150 ml of a nutrient medium having the same composition (g/l):

| | | | |
|---|---|---|---|
| $K_2HPO_4$ | — 0.5 | $KH_2PO_4$ | — 0.6 |
| $MgSO_4$ | — 0.5 | $FeSO_4$ | — 0.005 |
| $CoCl_2$ | — 0.01 | glucose | — 5 |
| $NaNO_3$ | — 1 | | |

The flask was incubated on a shaker for 48 hours at 30° C. The nitrile hydratase activity of the cells was determined using acrylonitrile as a substrate. The specific activity of the nitrile hydratase in the strain M33 reached 200 units/mg, its total activity being 360 units/ml.

Thus, the specific activity of the strain M33 cultivated in a urea-free medium is more than 60 times greater than the activity of the strain J1. What is more, commercially readily available components of the medium, namely, glucose and sodium nitrate, are used to grow the strain M33.

Example 2

Five ml of a culture of the strain M33 preliminarily grown for 48 hours at 30° C. in a medium of the same composition as in Example 1, with the exception that glucose was taken in an amount equal to 20 g/l and urea in an amount of 2 g/l was used instead of sodium nitrate, was introduced into an Erlemmeyer flask (750 ml volume) containing 150 ml of the same nutrient medium. The flask was incubated on a shaker at 30° C. for 48 hours. The nitrile hydratase activity was determined using acrylonitrile as a substrate. The cell yield was 7.6 g/l, specific activity—180 units/mg, total activity—1,386 units/ml.

Example 3

The strain M33 was grown using the same procedure as described. The cells were separated by centrifuging, washed with 10 mM of a phosphate buffer, and resuspended in a 10 mM of a phosphate buffer. Reaction was conducted under standard conditions using various nitriles as substrates. The reaction was discontinued by addition of concentrated HCl, the concentration of the amides thus-formed being determined by gas chromatography.

TABLE

| Substrate | Specific activity, %* |
|---|---|
| Acetonitrile | 140 |
| Acrylonitrile | 100 |
| 3-cyanopyridine | 54 |
| 4-cyanopyridine | 70 |
| 2-cyanopyridine | 22 |

*Specific activity with acrylonitrile used as a substrate (200 mcM/min/mg) taken as 100%.

It transpires from the table above that the strain M33 is capable of catalyzing hydrolysis of both aliphatic and aromatic nitriles.

Example 4

The strain M33 was grown as in Example 1. A biomass containing M33 cells up to a concentration of 0.5 mg/ml and 3-cyanopyridine up to a concentration of 8% was added into a 100-ml flask containing 40 ml of distilled water (pH 7.6). The flask was incubated at 30° C. under stirring conditions. After 60 minutes, a 10%-nicotinamide solution was obtained. Nicotinic acid and 3-cyanopyridine were not present in the reaction mixture.

Example 5

Into a steel reactor having a volume of 1.5 l and provided with a mechanical stirrer and thermostattable within the temperature range of from 12° to 20° C., 400 ml of distilled water were poured (pH 7.6), followed by resuspending in it 272 mg of a biomass (based on the dry matter content) of the strain of *Rhodococcus rhodochrous* M33 grown as described in Example 1. Then a pure acrylonitrile was added to the reaction mixture at such a rate that its concentration in the solution would not exceed 2%. The qualitative and quantitative compositions of the solution were determined by gas-liquid chromatography. All in all, 173 g of acrylonitrile were placed into the reactor. A 46% (weight/volume) solution of acrylamide was obtained after 8 hours. The yield of acrylamide was close to 99%. No acrylonitrile and acrylic acid were detected as by-products.

Thus, the claimed strain M33 has a high nitrile hydratase activity and is capable of hydrating both aliphatic and aromatic nitriles into corresponding amides. As distinct from its prior-art analogues, the mutant strain M33 is capable of constitutively producing nitrile hydratase when cultivated in media containing no inducers for synthesis of nitrile hydratase. This advantageous feature makes it possible to use media without vitamins, but containing glucose as a carbon source, and sodium (or potassium) nitrite as a nitrogen source, for cultivation of the cells. These media contain no special compounds as inducers of nitrile hydratase (such as amides, nitriles or urea taken in high concentrations). Another advantageous feature of the strain M33 resides in the virtually complete absence of amidase activity which blocks the formation of acids from the amides in the process of catalytically assisted conversion of the nitriles.

The strain *Rhodococcus rhodochrous* M33 can be recommended as a producer of a nitrile hydratase enzyme and it can be used in processes to prepare aliphatic and aromatic amides from nitriles.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

We claim:

1. An isolated culture of *Rhodococcus rhodochrous* VKM Ac-1515D, having the ability to produce nitrile hydratase.

2. A process for the production of nitrile hydratase comprising the steps of growing strain *Rhodococcus rhodochrous* VKM Ac-1515D in a suitable growth medium comprising a salt, a carbon source, and a nitrogen source and recovering the nitrile hydratase.

3. A method for the production of an amide from a nitrile comprising the steps of:

culturing a strain of *Rhodococcus rhodochrous* VKM Ac-1515D in a growth medium comprising a salt, a carbon source and a nitrogen source;

contacting said cultured strain with a nitrile to convert the nitrile into a corresponding amide; and isolating said amide from the medium.

4. The method according to claim 3, wherein said growth medium is free of an enzymatic inducer.

5. The method according to claim 3, wherein said growth medium is free of a vitamin.

* * * * *